United States Patent [19]

McGlave et al.

[11] Patent Number: 5,460,964
[45] Date of Patent: Oct. 24, 1995

[54] METHOD FOR CULTURING HEMATOPOIETIC CELLS

[75] Inventors: Philip B. McGlave; Catherine M. Verfaillie, both of St. Paul; Jeffrey S. Miller, Little Canada, all of Minn.

[73] Assignee: Regents of the University of Minnesota, Minneapolis, Minn.

[21] Appl. No.: 32,670

[22] Filed: Mar. 17, 1993

Related U.S. Application Data

[63] Continuation-in-part of Ser. No. 862,814, Apr. 3, 1992, abandoned.

[51] Int. Cl.$^6$ .................. C12N 5/02; C12N 5/06; C12N 5/08
[52] U.S. Cl. .................. 435/240.21; 435/240.1; 435/240.2; 435/240.241; 435/240.25
[58] Field of Search .................. 435/2, 7.24, 240.1, 435/240.2, 240.21, 240.241, 240.243, 240.25, 284

[56] References Cited

U.S. PATENT DOCUMENTS

| | | | |
|---|---|---|---|
| 4,342,828 | 8/1982 | Takaku et al. | 435/41 |
| 4,714,680 | 12/1987 | Civin | 435/240 |
| 4,721,096 | 1/1988 | Naughton et al. | 128/1 |
| 4,808,611 | 2/1989 | Cosman | 514/12 |
| 4,873,191 | 10/1989 | Wagner et al. | 435/172.3 |
| 4,902,783 | 2/1990 | Goda et al. | 530/415 |
| 4,946,437 | 8/1990 | Sredni et al. | 604/49 |
| 4,965,204 | 10/1990 | Civin | 435/240.27 |
| 5,004,681 | 4/1991 | Boyse et al. | 435/2 |
| 5,035,994 | 7/1991 | Civin | 435/2 |
| 5,061,620 | 10/1991 | Tsukamoto et al. | 435/7.21 |
| 5,104,804 | 4/1992 | Humphries et al. | 435/291 |
| 5,139,951 | 8/1992 | Butz et al. | 435/284 |
| 5,192,553 | 3/1993 | Boyse et al. | 424/529 |

FOREIGN PATENT DOCUMENTS

| | | |
|---|---|---|
| 341966 | 11/1989 | European Pat. Off. . |
| 395355 | 10/1990 | European Pat. Off. . |
| 455482 | 11/1991 | European Pat. Off. . |
| WO87/06120 | 10/1987 | WIPO . |

OTHER PUBLICATIONS

Greenberger in Hematopoiesis (ed. D. W. Golde) pp. 203–242 Churchill Livingstone N.Y. 1984.
Knapp et al. Leukocyte Typing IV, CD Guide, p. 1083 CD 34 (1992).
Wang et al. Ann NY Acad Sci 665: 274–284 (1992).
Koller et al. J Cell Biochem Suppl 16: 135 (1992).
Broxmeyer et al. Blood 76: 1110–1116 (1990).
Gluck et al. Exp Hematol 17: 398–404 (1989).
Caldwell J. Cell Physiol. 147: 344–353 (1991).
Testa ACTA Haematol 86: 122–127 (1991).
Dorshkind Ann Rev Immunol. 8:111–137 (1990).
Hurley et al. Blood 82: 21A, 1993.
Gupta et al. Blood 82: 21A, 1993.
Verfaillie et al. J Exp Med 179: 643–649 (1994).
Verfaillie Blood 82: 2045–2053 (1993).
Verfaillie Blood 79: 2821–2826 (1992).
L. Simonovitch, J. Cell. Comp. Physiol., 64 23 (1964).
T. M. Dexter et al., J. Cell Physiol., 91, 335 (1977).
R. Shields et al., J. Cell. Physiol., 91 345 (1977).
T. M. Dexter et al., J. Exp. Med., 145, 1612 (1977).
S. Gartner et al., PNAS USA, 77, 4756 (1980).
I. R. G. Toogood et al., Leukemia Res., 4, 449 (1980).
S. A. Bentley, Exp. Hematol., 9, 308 (1981).
F. T. Slovick et al., Exp. Hematol., 12, 327 (1984).
M. Y. Gordon et al., Internat. J. Cell Cloning, 1, 429 (1983).
W. W. Kwok et al., PNAS USA, 83, 4552 (1986).
I. R. Freshney, "Hemopoietic Cells," in *Culture of Animal Cells*, A. R. Liss, N.Y. (187) at pp. 284–288.
M. Y. Gordon et al., J. Cell. Physiol., 130, 150 (1987).
M. Y. Gordon et al., Nature, 326, 403 (1987).
T. Friedmann, Lancet, 1271 (Jun. 4, 1988).
G. J. Spangrude et al., Science, 241, 58 (1988).
J. Brandt et al., J. Clin. Invest., 82, 1017 (1988).
T. Friedmann, Science, 244, 1275 (1989).
I. Bertoncello et al., Exp. Hematol., 17, 171 (1989).
S. J. Szilvassy, PNAS USA, 86, 8798 (1989).
H. J. Sutherland et al., Blood, 74, 1563 (1989).
C. Verfaillie et al., J. Exp. Med., 172, 509 (1990).
M. A. S. Moore, Cancer Surveys, 9, 7 (1990).
D. M. Bodine, Ann. N.Y. Acad. Sci., 612, 415 (1990).
D. Zipori et al., Exp. Hematol., 8, 816 (1990).
P. M. Lansdorp et al., J. Exp. Med., 172, 363 (1990).
R. G. Andrews et al., J. Exp. Med., 172, 355 (1990).
H. H. Gerhartz et al., Blood, 76, 274a, Abstract 1087 (1990).
H. J. Sutherland et al., PNAS USA, 87, 2584 (1990).
J. Brandt et al., J. Clin. Invest., 86, 932 (Sep. 1990).
B. D. Luskey et al., Annal. N.Y. Acad. Sci., 612 398 (1990).
L. W. M. M. Terstappen et al., Blood, 77, 1218 (Mar. 1991).
R. M. Lemoli et al., Blood, 77, 1829 (Apr. 15, 1991).
E. Bruno et al., Blood, 77, 2339 (Jun. 1, 1991).
J.-H. Shieh et al., J. Immunol., 147, 2984 (1991).
C. M. Verfaillie et al., Blood, 77, 263 (1991).
H. J. Sutherland et al., Blood, 78, 666 (1991).
C. Smith et al., Blood, 77, 2122 (May 15, 1991).
M. A. S. Moore, Blood, 78, 1 (Jul. 1, 1991).
M. A. S. Moore, Cancer Supp., 2718 (May 15, 1991).
R. M. Schwartz, PNAS USA, 88, 6760 (Aug., 1991).
E. F. Srour et al., Blood Cells, 17, 287 (1991).
C. C. Fraser et al., PNAS USA, 89, 1968 (Mar. 1992).
C. M. Baum et al., PNAS USA, 89, 2804 (Apr. 1992).
Costar "Transwell" Tech Data Sheet (no date).
Transplantation, vol. 48, issued Oct. 1989, A. H. Frankel et al., "Requirements for the Induction of Allospecific CD8+ Suppressor T Cells in the Rat Primary Mixed Lyumphocyte Response", pp. 639–646.

*Primary Examiner*—David L. Lacey
*Assistant Examiner*—Phillip Gambel
*Attorney, Agent, or Firm*—Schwegman, Lundberg & Woessner

[57] ABSTRACT

A method for culturing mammalian hematopoietic, preferably stem cells, is provided comprising maintaining a population of human hematopoietic cells in a non-contacting relationship to a population of cultured stromal cells, which populations are in preferably liquid stromal growth medium connection, so that the ability of the stem cells in said population to differentiate and self-replicate is maintained during an extended culture period.

18 Claims, 3 Drawing Sheets

METHOD FOR CULTURING HEMATOPOIETIC CELLS

This invention was made with the support of NIH grant number RO1-CA-45814-01. The Government has certain rights in the invention.

CROSS REFERENCE TO RELATED APPLICATION

This application is a continuation-in-part of U.S. patent application Ser. No. 7/862,814 filed Apr. 3, 1992, now abandoned.

BACKGROUND OF THE INVENTION

The human hematopoietic system is populated by cells of several different lineages. These "blood cells" may appear in bone marrow, the thymus, lymphatic tissue(s) and in peripheral blood. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocytes, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages.

Assignment of cell to lineage and to a maturational stage within a cell lineage indicates lineage commitment. There are cells, however, which are uncommitted to any lineage (i.e., the "progenitor" cell) and which, therefore, retain the ability to differentiate into each lineage. These undifferentiated, pluripotent progenitor cells will hereinafter be referred to as the "stem cells."

Therefore, all of mammalian hematopoietic cells can, in theory, be derived from a single stem cell. The stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding a mature cell.

The benefit of obtaining a pure population of stem cells is most readily recognized in the field of gene therapy. Briefly, gene therapy can be used to treat specific diseases caused by a defect in a particular gene. For example, sickle cell anemia is caused by a defect in a single gene. The red blood cells of sickle cell patients contain this defective gene which, in turn, codes for a defective form of the protein hemoglobin. The defective form results in the clinical condition of sickle cell anemia. Sickle cell anemia cannot be "cured" by conventional drug therapies because the underlying defect is in the gene which is included within every cell.

Gene therapy seeks to replace or repopulate the cells of the hematopoietic system with cells that do not contain the defective gene but instead contain a "normal" gene. Using conventional recombinant DNA techniques, a "normal" gene is isolated, placed into a viral vector, and the viral vector is transfected into a cell capable of expressing the product coded for by the gene. The cell then must be introduced into the patient. If the "normal" gene product is produced, the patient is "cured" of the condition. The difficulty is that the transformed cells must be capable of continual regeneration as well as growth and differentiation.

Kwok et al., *PNAS USA*, 83, 4552 (1986), successfully demonstrated that gene therapy was possible using progenitor cells in dogs. Kwok et al. incorporated certain genes into the equivalent of lineage committed cells by retroviral transfection using standard recombinant DNA techniques and transplanted the transfected cells into the dogs. They obtained expression of the gene product(s) in cells isolated from the dogs. While the cells used by Kwok et al. are capable of growth and differentiation, they are not capable of self-renewal. Thus, any "cure" would be temporary. Stem cells, however, provide a better choice of cells in which to tranfect or otherwise insert a vector containing a "normal" gene. Stem cells have the capability not only of differentiating into cells of every lineage but also of self-renewal, thus establishing an unlimited supply of such cells. Therefore, by transplanting a stem cell, cells of every type in the hematopoietic system containing the "normal" gene will be continuously provided.

However, stem cells are usually in a resting state, which lowers the efficiency of transfection. Also, one of the most effective methods for viral transfection of hematopoietic cells known thus far is co-cultivation of the target cells with "high titer, virus-producing cell lines." These virus-producing cell lines are often derived from other species, such as the mouse. Infusion of a human patient with a transfected stem cell population contamination by virus-producing cell lines, especially those derived from another species, is objectionable.

Furthermore, substantial problems have been encountered in (a) identifying the antigenic markers unique to stem cells, (b) isolating homogenous populations comprising substantial numbers of non-lineage committed, pluripotent stem cells and (c) maintaining and, possibly, expanding populations of human stem cells.

Difficulties are also presented by the fact that the stem cell population constitutes only a small percentage of the total number of leukocytes in bone marrow. I. L. Weissman et al. have reported that murine bone marrow cells contain only about 0.02–0.1% pluripotent stem cells. This group reported that Thy-1$^{lo}$Lin$^-$Sca2-1$^-$murine bone marrow cells are a "virtually pure population of primitive myeloerythroid stem cells." Only 20–30 of these cells were sufficient to rescue one-half of a group of lethally-irradiated mice. See, Stanford University (published European Patent Application No. 341, 966), and G. J. Spangrude et al., *Science*, 241, 58 (1988).

However, at the present time it is not known which antigens are present on stem cells alone or are also present on more differentiated progenitors. As in mice, one marker which has been indicated as present on human stem cells, CD34, is also found on a significant number of lineage committed progenitors. Another antigen which has been reported to provide for some enrichment of progenitor activity is Class II HLA (particularly a conserved DR epitope recognized by a monoclonal antibody designated J1–43). However, these markers are also found on numerous lineage committed hematopoietic cells. The Thy-1 molecule is a highly conserved protein present in the brain and in the hematopoietic system of rat, mouse and man. These species differentially express this antigen and the true function of this molecule is unknown. However, the Thy-1 molecule has been identified on rat and mouse hematopoietic stem cells. This protein is also believed to be present on most human bone marrow cells, but may be absent on stem cells.

Recently, a number of research groups have reported the use of these and other markers to isolate populations of mammalian bone marrow cell populations which are enriched to a greater or lesser extent in pluripotent stem cells. For example, in U.S. Pat. No. 4,714,680, Civin describes a differentiation antigen which is recognized by the monoclonal antibody designated My-10. In normal (i.e., nonleukemic) individuals, this antigen is found on progenitor cells within the hematopoietic system. Accordingly, Civin has described a population of progenitor stem cells which express the antigen recognized by My-10 (i.e., express the CD34 antigen), and has described a method of using My-10 to isolate stem cells for bone marrow transplantation. My-10 has been deposited with the American Type Culture Collection (Rockville, Md.) as HB-8483. My-10 is commercially available from Becton Dickinson Immunocytometry Systems ("BDIS") as anti-HPCA 1. However, using an anti-CD34 monoclonal antibody alone is not sufficient to distinguish between "stem cells," as described by Civin, and the true pluripotent stem cell, since B cells ($CD19^+$) and myeloid cells ($CD33^+$) make up 80–90% of the $CD34^+$ population.

More recently, Becton Dickinson and Company (published European Patent Application No. 455,482) claimed a "substantially pure population of human cells containing pluripotent stem cells that express the CD34 antigen but lack expression of the CD38 antigen and other lineage associated antigens." To isolate this population of human pluripotent stem cells, a combination of anti-CD34 and anti-CD38 monoclonal antibodies are used to select those human progenitor stem cells that are $CD34^+$ and $CD38^-$. One method for the preparation of such a population of progenitor stem cells is to stain the cells with immuno-fluorescently labelled monoclonal antibodies. The cells then may be sorted by conventional flow cytometry wherein those cells that are $CD34^+$ and those cells that are $CD38^-$ are selected for. Upon sorting, a substantially pure population of stem cells is reported to result.

Tsukamoto et al. (U.S. Pat. No. 5,061,620) disclose a method for the negative selection of differentiated and "dedicated" cells from human bone marrow to yield a population comprising "human hematopoietic stem cells with fewer than 5% lineage committed cells." The stem cells are characterized as being "for the most part" $CD34^+$, $CD3^-$, $CD7^-$, $CD8^-$, $CD10^-$, $CD14^-$, $CD15^-$, $CD19^-$, $CD20^-$, $CD33^-$, Class II $HLA^+$ and $Thy-1^+$.

C. Verfaillie et al., J. Exp. Med., 172, 509 (1990) reported that a two-step purification of low density human bone marrow cells by negative immunomagnetic selection and positive dual-color fluorescence activated cell sorting (FACS) yielded a $Lin^-CD34^+HLA/DR^-$ cell fraction that was 420-fold enriched in pluripotent stem cells capable of initiating long-term bone marrow cultures (LTBMC); over unmanipulated bone marrow mononucleocytes (BMMNC) obtained after Ficoll-Hypaque separation. This group reported that the combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that previously reported.

The development of cell culture media and conditions that will maintain stem cells in vitro for the extended periods of time required for the procedures involved in gene therapy, identification of growth factors, thorough characterization of cell morphologies and the like, has presented a unique set of obstacles. To date, successful in vitro stem cell cultures have depended on the ability of the laboratory worker to mimic the conditions which are believed to be responsible for maintaining stem cells in vivo.

For example, hematopoiesis occurs within highly dense cellular niches within the bone marrow in the adult and in similar niches within the fetal yolk sac and liver. Within these niches, stem cell differentiation is regulated, in part, through interactions with local mesenchymal cells or stromal cells. Mammalian hematopoiesis has been studied in vitro through the use of various long-term marrow culture systems. T. M. Dexter et al., in J. Cell Phyiol., 91, 335 (1977) described a murine system from which spleen colony-forming units (CFU-S) and granulocyte/-macrophage colony forming units (CFU-GM) could be detected for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone marrow. Human long-term culture systems were reported to generate assayable hematopoietic progenitor cells for 8 or 9 weeks, and, later, for up to 20 weeks (See, S. Gartner et al., PNAS USA, 77, 4756 (1980); F. T. Slovick et al., Exp. Hematol., 12, 327 (1984)). Such cultures were also reliant on the preestablishment of a stromal cell layer which must frequently be reinoculated with large, heterogeneous populations of marrow cells. Hematopoietic stem cells have been shown to home and adhere to this adherent cell multi-layer before generating and releasing more committed progenitor cells (M. Y. Gordon et al., J. Cell. Physiol., 130, 150 (1987)).

Stromal cells are believed to provide not only a physical matrix on which stem cells reside, but also to produce membrane-contact signals and/or hematopoietic growth factors necessary for stem cell proliferation and differentiation. This heterogeneous mixture of cells comprising the adherent cell layer presents an inherently complex system from which the isolation of discrete variables affecting stem cell growth has proven difficult. Furthermore, growth of stem cells on a stromal layer makes it difficult to recover the hematopoietic cells or their progeny efficiently.

Recently, J. Brandt et al., in J. Clin. Invest., 86, 932 (1990), reported the maintenance of hematopoiesis of $CD34^+$, $DR^-$, $CD15^-$, $CD71^-$ human marrow cells in liquid culture for up to 8 weeks, when the culture was supplemented with 48-hourly additions of recombinant IL-1α, IL-3, IL-6 or granulocyte/macrophage colony-stimulating factor (GM-CSF). The establishment of an adherent cell layer was not observed, but cultures containing no exogenous cytokines produced clonogenic cells for only one week. However, even with the optimal cytokine combinations evaluated by Brandt et al., the progenitor cell (blast) population declined throughout the lifetime of these cultures, so that it is not clear that stem cell survival or proliferation is supported by this methodology.

Therefore, a need exists for methods for the long-term in vitro culture of human hematopoietic cells, including human stem cells.

SUMMARY OF THE INVENTION

The present invention provides a method for the long-term culture of mammalian, preferably murine or human, hematopoietic cells. As used herein, the term "hematopoietic cells" includes both the uncommitted, pluripotent "stem cells" described above, as well as the lineage-committed, or dedicated, progenitor cells which can develop into mature "blood cells" and mixtures thereof. Thus, the present method is effective to maintain the stem cell population in a population of hematopoietic cells such as the 34$^+$Lin$^-$DR$^-$marrow cell population and the less selected CD34$^+$enriched population described above. The ability of the present method to maintain and/or expand the population of stem cells within a cell population can be evaluated by determining the continuing presence/number of cells capable of initiating long-term bone marrow cultures (LTBMC-IC). The presence of these cells after at least five weeks of culturing a given population of cells provides art-recognized confirmation that stem cells have been preserved and/or expanded.

The present method is also effective to derive and expand committed progenitors both from such stem cell populations, as well as from already committed progenitor cells, such as those from sources such as human bone marrow, human newborn cord blood, fetal liver and adult human peripheral blood. The existence and number of committed progenitors can be determined by assaying for colony-forming cells (CFC) as disclosed hereinbelow.

A preferred embodiment of the present method comprises maintaining a population of hematopoietic cells in a fixed, non-contacting relationship to a population of cultured mammalian stromal cells, i.e., human or murine stromal cells or cell lines, which populations are preferably in liquid stromal cell growth medium connection during culturing.

Preferably, the populations are both human and allogeneic, most preferably they are autologous, although they need not be. For example, the stromal cell population and the hematopoietic cell population are preferably adhered to, or supported by, discrete cell culture substrata, which substrata are immersed in a stationary or flowing body of stromal cell culture medium.

Thus, the present method at least substantially conserves the stem cell population throughout the culturing period, while preserving, and preferably enhancing, its ability to differentiate into lineage-committed progenitor cells (hereinafter referred to as "committed progenitors"). The present method can also be used to derive and expand committed progenitors (CFC) from already committed progenitor cell populations. As used herein, the term "stromal cells" includes (1) human allogeneic or autologous stromal cells, or non-human stromal cells, (2) human or non-human stromal cell lines, and (3) human or non-human virally infected cell lines, such as immortalized embryonic fibroblasts which are effective to provide "feeder layers" for stem cell populations.

The present method also greatly facilitates the characterization and isolation of cultured human stem cells, or of more various hematopoietic cell populations containing said stem cells but not containing a stromal cell "feeder layer," since the method does not employ direct contact between the stromal cell layer and the hematopoietic cells. Furthermore, while prior culture methods for hematopoietic cells which do not employ contact layers of stromal cells can only maintain viable hematopoietic cells for about 2–3 weeks in the absence of added cytokines, the present method can maintain viable populations of normal human stem cells for at least 5 weeks in the absence of added cytokines. Preferably, the present system can be maintained for up to six months or more.

Although in the absence of added cytokines, the absolute number of stem cells declines over time, the number of stem cells remaining at five weeks is greater than that obtained using prior art methods in which hematopoietic cells are grown in direct contact with stroma or than that described in the prior art when hematopoietic cells are grown in cytokine-augmented media not containing stromal cells. For example, in accord with the present method, about 40–50% of the initial stem cell population can be preserved after 5 weeks, without added cytokines. However, added cytokines have been found to stimulate or enhance cell expansion, production of committed progenitors as measured by the presence of colony-forming cells (CFC) and the generation and conservation of LTBMC-IC in some cases. Such cytokines include interleukin-3 (IL-3), macrophage inflammatory protein (MIP-1$\alpha$), and, most preferably, combinations thereof.

For example, the addition of IL-3 alone and in combination with MIP-1$\alpha$ to the 34$^+$Lin$^-$DR$^-$marrow cell population described above, when cultured in liquid contact with cultured stromal cells via stromal cell culture medium, resulted in significantly greater cell expansion and generation of committed progenitors (CFC) than did cytokine-free cultures. While the culture of the cells for five weeks in cytokine-free stromal cell culture medium liquid contact resulted in a 58% loss of LTBMC-IC, addition of IL-3 to the medium resulted in an increase in LTBMC-IC recovery after five weeks of culture, compared with cytokine-free culture. Surprisingly, addition of both IL-3 and MIP-1$\alpha$ resulted in greater recovery of LTBMC-IC as compared to non-supplemental cultures. Moreover, the absolute number of LTBMC-IC present in cells recovered from IL-3 plus MIP-1$\alpha$ supplemented cultures was either equivalent to or greater than that present in the initial 34$^+$Lin$^-$ DR$^+$stem cell population. Therefore, the present invention provides the first method which is capable of both conserving and expanding stem cells (LTBMC-IC) in vitro.

The present invention also provides an improved method for culturing a population of hematopoietic cells employing sequential additions of stromal cell culture medium which has been preconditioned by culturing stromal cells therein. Thus, the present invention provides an improved method of culturing hematopoietic cells using stromal cell-conditioned medium, comprising:

(a) establishing a culture of stromal cells in a volume of liquid stromal cell culture medium;

(b) essentially simultaneously establishing a culture of hematopoietic cells in hematopoietic cell culture medium;

(c) withdrawing a preselected volume of stromal cell culture medium effective to stimulate the growth of the culture of hematopoietic cells and replacing an equivalent volume of the liquid hematopoietic cell culture medium with the preselected volume of stromal cell culture medium;

(d) replenishing said volume of liquid stromal culture medium with fresh exogenous liquid stromal culture medium; and (e) repeating steps (c)–(d) at intervals of about 16–32 hours so as to expand said culture of hematopoietic cells.

Preferably, the amount of stromal cell culture medium withdrawn in step (c) is a minor amount (5–20%) of the total amount, and is withdrawn at about 24-hour intervals (or once a day). Preferably, steps (c)–(d) are repeated at regular intervals for at least about a week (168 hours). After about one week, preferably about 50–90% of the original hematopoietic cell medium can be replaced by the stromal cell-conditioned medium. At this point, after about one week, preferably about 40–60% of the stromal cell culture medium is replaced by fresh, exogenous stromal cell culture medium, and steps (c)–(e) of the culture process can be continued indefinitely in about 7-day cycles. As shown in the working examples, hematopoietic cells can be cultured in accord with this method about as, or more effectively, than via the "stromal-non-contact" method using a continuous liquid culture medium contact between the stromal cells and the hematopoietic cells, such as an enriched stem cell population.

This embodiment of the invention can employ the same classes of stromal "feeder" cells, culture substrates, medium, cytokines, and hematopoietic cells as can the continuous liquid contact embodiment of the invention. It is advantageous in that it does not require complex equipment or instrumentation, but does require more manual manipulations than the continuous liquid contact method.

The present invention also comprises a population of self-replicating stem cells prepared in accord with the present method, e.g., free of a stromal cell feeder layer, which are preferably $Lin^-CD34^+DR^-$. Unexpectedly, it was also found that the number of committed progenitors increases markedly during the culture period. Although not intending to be bound to any theory of action, it is believed that this effect may be due to removal of the population of stem cells from direct contact with the stromal cells which, in turn, may lift the negative regulation of the stem cell population which is necessarily operative in vivo. The invention also provides an improved method for expanding the population of committed progenitors over that present in the initially cultured population, while maintaining or conserving a population of self-replicating, pluripotent stem cells.

DETAILED DESCRIPTION OF THE INVENTION

One hematopoietic cell population which can be cultured in accord with the present methods can be derived from mammalian bone marrow, as from human bone marrow, e.g., by centrifugation and the immunomagnetic and FACS procedures as described in C. Verfaillie et al., *J. Exp. Med.*, 172, 509 (1990) (hereinafter "C. Verfaillie et al."). This procedure yields cell populations highly-enriched in human stem cells which are characterized by being $Lin^- CD34^+DR^-$. Other hematopoietic cell populations enriched stem cells include the $CD34^+$ population disclosed by Civin (U.S. Pat. No. 4,714,680), the $CD34^+$, $CD38^-$ population disclosed in European patent application No. 455,482, and the population disclosed by Tsukamato et al. (U.S. Pat. No. 5,061,620).

Allogeneic mammalian stromal cells can be obtained as described by T. M. Dexter et al., *J. Exp. Med.*, 145, 1612 (1977), and are preferably irradiated to eliminate contaminating cells, and subcultured on the present substrata (e.g., in plastic cell culture wells) as described in C. Verfaillie et al., or as by J. Caldwell et al., *J. Cell. Phys.*, 147., 344 (1991). Murine stromal cell lines are also available to the art, e.g., from the American Type Culture Collection, Rockville, Md.

Figure 1:
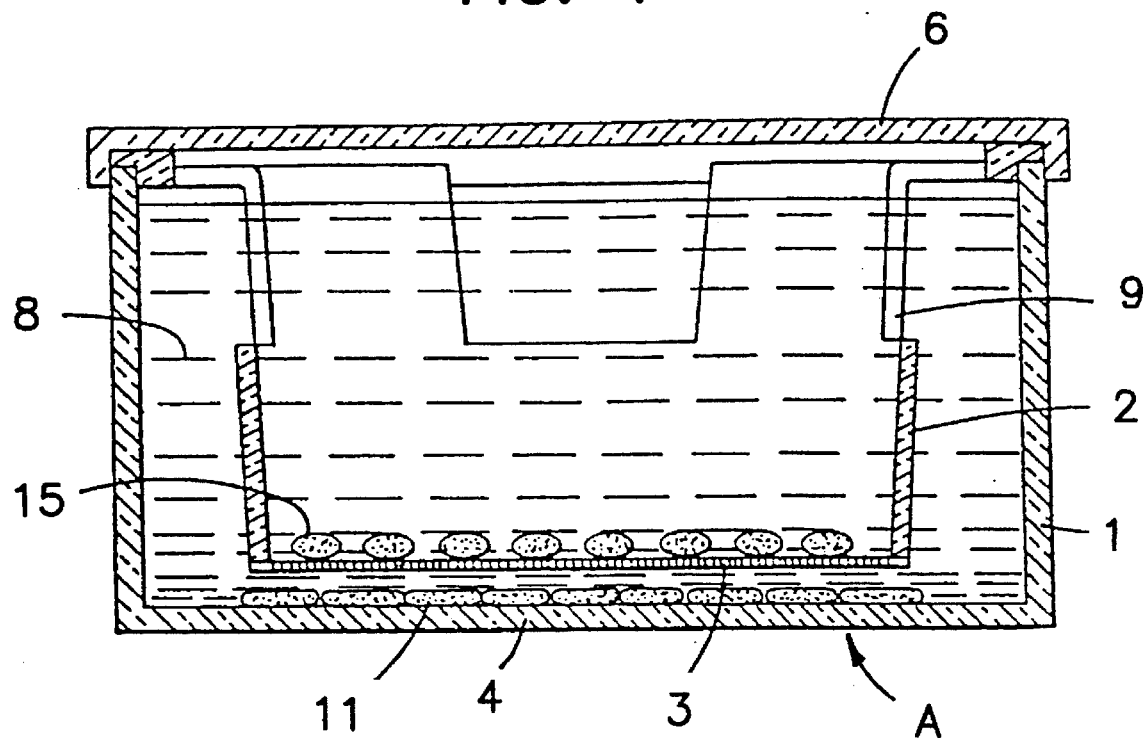
FIG. 1 is a schematic cross-sectional view of a cell culture chamber useful in the present method.

Preferably, the hematopoietic cell population is supported by a culture substratum such as a microporous hollow fiber or on a microporous membrane which maintains the hematopoietic cells and any associated cells in liquid medium contact with the stromal cell population. The stromal cell population can also be supported on a similar discrete substratum. Preferably, a microporous membrane separates the two populations, e.g., by about 0.25–2.0 mm, as shown in FIG. 1. The pores of the membrane or the hollow fibers can vary in size, so long as they allow culture medium and its components to contact the hematopoietic cells, while avoiding stromal cell contact and providing adequate support for the hematopoietic cells. The hematopoietic cells may also be attached to the interior of a microporous tube or hollow fiber, while the stromal cells are maintained in a fixed relationship from the exterior of the tubing, e.g., on the walls of a chamber containing the growth medium. Preferably, the microporous membrane or the hollow fibers are formed of a synthetic polymer, which can be coated with a cell-adherence promoting peptide, such as mammalian (human) collagen, laminin, fibronectin or the subunits thereof possessing the ability to promote hematopoietic cell attachment. For example, such peptides are disclosed in U.S. Pat. Nos. 5,019,546, and 5,059,425.

During the practice of the present method, the liquid growth medium may be held as a stationary body which envelops both populations of cells, and is preferably about 25–100% exchanged at fixed intervals, e.g., of 8 hrs–14 days, preferably of about 0.5–10 days. Such regular exchanges of stromal cell growth medium have been reported to enhance the production of endogenous growth factors, such as granulocyte/macrophage colony stimulating factor (GM-CSF), from stromal cells, by J. Caldwell et al., *J. Cellular Phys.*, 147,344 (1991). As described above, the population of hematopoietic cells can also be cultured in a discrete, separate culture vessel, in medium which is supplemented by sequential additions of stromal cell culture medium which has been preconditioned by culturing stromal cells therein. Such a method does not employ continuous liquid contact between the two cell populations.

Alternatively, the culture medium can be continuously circulated through a culture chamber that contains the hematopoietic cells and the stromal cells, and replaced/replenished at a site remote from the culture chamber. Alternatively, the hematopoietic cells and the stromal cells can be cultured in separate cell culture chambers, e.g., on the exterior surfaces of bundles of microporous hollow fiber bundles contained in separate chambers, so long as they remain in circulating stromal cell culture medium liquid connection, e.g., via tubing connecting the chambers to each other and to a reservoir of stromal cell culture medium.

One commercially available device that contains discrete and separable cell culture substrata for both the stromal cell population and the hematopoietic cell population is the Transwell™ series of cell culture chambers available from Costar Corp., Cambridge, Md., USA. As depicted in schematic cross-section in FIG. 1, each Transwell® chamber (A) comprises a flat-bottomed plastic lower compartment 1, and a plastic upper compartment 2, which can be removably inserted into compartment 1, so that the collagen-coated, microporous membrane 3 (0.45 μm pore diameter), which forms the bottom of compartment 2, is held in a fixed, essentially parallel relationship to the inner surface of the bottom (4) of the compartment. This assembly is covered by a removable lid 6. In use, stroma cells 11 are added to the bottom of lower compartment 1, and a preselected amount of liquid culture medium 8 is added. Stem cells or other hematopoietic cells, 15, are added to the upper surface of microporous membrane 3 and the upper compartment (or transwell) 2 is inserted into the lower compartment. Opening 9 in the sidewall of the transwell 2 permits addition of or removal of the medium 8 from the exterior void space of the chamber A. The cover 6 is then replaced. Following the culture period, which can be as long as 3–6 months, the cover 6 is removed; the transwell is removed, and all or a portion of the stem cells or other hematopoietic cells 15 are then removed from the microporous membrane and employed in the end use.

For example, the stem cells or other hematopoietic cells may be used in bone marrow transplantation to repopulate the bone marrow of a patient such as a myeloid or lymphoid leukemia patient whose "defective" marrow has been destroyed by lethal irradiation, chemotherapy, or other agents causing aplasia without recovery. For example, the ability to cultivate large numbers of committed progenitors from stem cells to be used for transfusion therapy may be particularly useful in circumstances where it can be foreseen that a patient will require blood products support, such as when there are impending plans to administer high-dose chemotherapy, or in the case of autologous bone marrow transplantation following lethal irradiation. Under these circumstances, it may be useful to cultivate and store the patient's own (autologous) population of committed progenitors before initiating chemotherapy in order to avoid the need for transfusion of blood products obtained from allogeneic donors. Culture of autologous stem cells or committed progenitors in the Transwell system or variants of this system allow the cultivation of a population of committed progenitors which, when transfused into the recipient, can be expected to have the following attributes:

1) Committed progenitors, unlike granulocytes and platelets currently used for transfusion, can be frozen and stored indefinitely. These features are particularly important in the case of granulocyte support since granulocytes from allogeneic donors are difficult to obtain, cannot be frozen, have a stored shelf life of less than 24 hours, and have a half-life of less than five minutes after transfusion into an allogeneic recipient.

2) The committed progenitors derived from cultured stem cells provide a sustained and long-lasting population of red blood cells, granulocytes and/or platelet precursors which mature in vivo after transfusion and can be expected to have a considerably longer half-life than mature blood products obtained from normal donors.

3) The cultivation of committed progenitor populations from autologous stem cells in accord with the present method, prior to an anticipated need for transfusion, obviates the need to locate, type (cross match) and phlebotomize normal, volunteer blood donors.

4) Use of cultivated, autologous committed progenitors also obviates the need for extensive ABO typing and safety monitoring, the risk of donor/-recipient transfusion reactions, the risk of infection with HIV, CMV, hepatitis viruses and other blood-borne infections associated with current donor/recipient blood product transfusion methods.

5) This approach will also provide adequate blood support in the case of individuals with rare ABO blood types for whom suitably matched donors cannot be located in a timely fashion or at all.

6) Cultivation of autologous committed progenitors will also eliminate the problems of recipient "sensitization" to allogeneic blood products commonly seen in patients receiving multiple transfusions.

7) Use of committed progenitors will also reduce the frequency of blood transfusions compared to use of allogeneic, mature blood products since committed progenitors cultivated in accord with the present invention can be expected to have a considerably longer half-life than blood components obtained from normal allogeneic donors, as discussed above.

Although it is currently envisioned that the present method would be primarily used for cultivation of autologous committed progenitors or mature blood cells prior to an anticipated need for blood component support, it is also believed that the present method can be used to cultivate a committed progenitor population suitable for transfusion from normal donors to allogeneic recipients. Thus, stem cells or committed progenitors from normal donors known to be free of infection could be cultivated to produce large quantities of committed progenitors or mature blood cells. The committed progenitors are suitable for long-term storage and subsequent transfusion into allogeneic recipients. This may be particularly useful when stem cells from donors of known rare blood types are cultivated and stored. Therefore, the present method may lead to the elimination of the current cumbersome, expensive and sometimes dangerous practices involved in the collection and transfusion of mature blood components from human donors.

The stem cells may also be used in gene therapy wherein a gene producing a protein, enzyme or other product is inserted into the DNA of the stem cells which are then transplanted into a patient's bone marrow. See, for example, B. P. Luskey et al., *Annals. N. Y. Acad. Sci.*, 612, 398 (1990) and B. A. Naughton et al. (U.S. Pat. No. 4,721,096).

To effect gene therapy with a substantially pure population of human stem cells, the following general method may be used to insert a gene into these progenitor cells. For a review of the methodologies that are applicable, see Friedman, *Science*, 244, 1275 (1989) and *Lancet*, Jun. 4, 1988, p. 1271. In order to introduce a normal gene, a normal gene is first isolated from the cells of a donor. The cells may be isolated from tissue(s), blood or other body fluids, including bone marrow. To find a gene coding for the defective protein, DNA from the donor cells is isolated and cleaved by enzymatic digestion into segments of varying length by means known to those skilled in the art. The segments of DNA then may be inserted individually into vectors containing the appropriate regulatory sequences for expression of a gene product. The vectors then can be screened by conventional means such as Northern blotting if the sequence for the normal gene is known or the expression product can be screened by Western blotting.

Alternatively, if the DNA sequence of the desired gene or the sequence of the normal protein is known, the gene can be made by synthetic chemistries such as on a DNA synthesizer (Applied Biosystems). In any case, the method of isolation or construction of the gene sequence can yield a "normal" gene that codes for the desired gene product.

Once the DNA containing the gene is prepared, the DNA can be inserted into the population of stem cells isolated as above. The DNA can be inserted by 1) physical methods such as coprecipitation with calcium phosphate, electroporation or microinjection (e.g., U.S. Pat. No. 4,873,191), and/or by 2) the use of viral vectors such as adenoviruses, if the DNA is less than approximately 7–8 kB, or retroviruses for longer segments of DNA. In the latter case, the DNA of the retrovirus is cut with a restriction enzyme and the human DNA containing the desired sequence is inserted and ligated. The retrovirus containing the insertion then is transfected into the stem cells. The stem cells then can be assayed for production of the desired protein. See, e.g., U.S. Pat. No. 4,902,783.

In general, molecular DNA cloning methods are well known in the art and are not limiting in the practice of this invention. For a further description of similar methods, see Friedmann, *Science*, 244, 1275 (1989) and *Molecular Cloning: A Laboratory Manual* (2nd ed.), Cold Spring Harbor Laboratory Press, Sambrook, Fritsch and Maniatis eds. (1989).

To transplant the stem cells containing the desired gene, the cells may be introduced into the bone marrow of the patient by conventional means of bone marrow transfer. Typically, this involves the delivery of the cells by intravenous infusion over a period of time. The bone marrow of the patient may be lethally irradiated prior to infusion to assure that the transplanted stem cells fully replace the existing bone marrow cells.

The present method of culturing stem cell populations can facilitate gene therapy in a number of ways:

1) Stem cells are usually in a resting state. Gene insertion (transfection) is performed more efficiently when cells are in cycle. Culture of the stem cell population in accord with the present method stimulates cycling of the stem cells and can be expected to increase the efficiency of transfection.

2) Growth of stem cells on a stromal layer makes it difficult to recover the hematopoietic stem cells or their progeny efficiently. Cultivation of stem cells via the present method allows complete and efficient recovery of the stem cell population and its progeny simply by removal of the supported stem cells from the system.

3) Currently, one of the most efficient methods for transfection of cells is co-cultivation of the target cells with "high titer, virus-producing cell lines." These virus-producing cell lines are often derived from other species such as the mouse. Patient infusion with a transfected stem cell population contaminated by virus-producing cell lines, especially those from another species, is objectionable. The present method allows recover of stem cells and their progeny which have been exposed to the high titer virus-producing cell line without contamination of the stem cell population by these foreign cell lines.

The invention will be further described by reference to the following detailed examples, wherein human bone marrow was obtained from 22 healthy young volunteers after informed consent by aspiration from the posterior iliac crest in preservative free heparin. Bone marrow mononuclear cells (BMMNC) were obtained after Ficoll-Hypaque separation (Sigma Diagnostics, St. Louis, MO) (s.g. 1.077).

Bone marrow mononuclear cells (BMMNC) were purified further in an initial counterflow elutriation step, by suspending BMMNC in PBS supplemented with 0.3% BSA (Sigma) and 0.01% EDTA (Sigma). The cells were injected into an elutriator system with standard separation chamber (Beckman Instruments, Inc., Palo Alto, Calif.) primed with Iscove's Modified Dulbecco's Medium (IMDM), 5% fetal calf serum (FCS) and 0.01% EDTA. Rotor speed and temperature were maintained at 1,950 RPM and 10° C. After loading, 200 ml of effluent was collected at a flow rate of 14 ml/min. The rotor was then stopped and the remaining BMMNC flushed from the separation chamber. Cells collected in fraction 14 were then depleted from T-lymphocytes and NK cells by sheep erythrocyte rosetting as described by C. M. Verfaillie et al., *Blood*, 77,263 (1991). Further depletion of committed lymphoid and myeloid/monocytic cells was obtained by negative immunomagnetic depletion of cells expressing CD2, CD3, CD11$b$, CD19, CD56, CD71, MY8 and glycophorin-A antigens using the methods described in C. Verfaillie et al.

The resultant lineage negative (Lin$^-$) cells were labeled with anti-CD34 and anti-HLA-DR antibodies as described by C. Verfaillie et al. Cells were sorted on a FACS-Star-Plus laser flow cytometry system (Becton-Dickinson, Mountain View, Calif.) equipped with a Consort 40 computer. Cells were initially selected for low vertical and very low/low horizontal light scatter properties. Cells selected in the first window expressing high numbers of CD34 antigens and lacking HLA-DR antigen expression were then sorted to yield DR$^-$cells, as described by C. Verfaillie, et al. These DR$^-$cells correspond to the highly stem cell-enriched population designated as Lin$^-$ 34$^+$DR$^-$in C. Verfaillie et al. The latter windows were chosen on the basis of the fluorescence pattern of control samples labeled with mouse IgG1-PE and mouse IgG2$a$-FITC antibodies.

Example 1. In Vitro Culture of DR$^-$Stem Cells

The DR$^-$cells were cultured as follows:

1. "Stroma-Free" cultures: 2–8×10$^3$/ml DR$^-$ cells were plated in complete media in wells of 24 (1 ml) or 6 well plates (4 ml) (Costar, Cambridge, Md.). No stromal layers were established. No cytokines were added to the complete media. The culture media consisted of IMDM with 12.5% fetal calf serum (HyClone Laboratories, Logan, Utah), 12.5% horse serum (HyClone Laboratories), 2 mM L-glutamine (Gibco Laboratories), penicillin 1,000 U/m and streptomycin 100 U/ml (Gibco) and 10$^{-6}$6M hydrocortisone (A-Hydrocort) (Abbott Laboratories, North Chicago, Ill.).

2. "Stroma-contact" cultures: Irradiated stromal cells were subcultured in 6 well (2×10$^6$ cells suspended in 4 ml) or 24 well (0.5×10$^6$ cells suspended in 1 ml) plates. DR$^-$cells (2–8×10$^3$/ml) were then plated onto the irradiated allogeneic stromal layers as described C. Veraillie et. al. (FIG. 1B).

3. "Stroma-non-contact" cultures: Transwell™ cultures consisted of allogeneic irradiated stromal cells derived from the same donors as the stromal cells used in the "stroma-contact" cultures subcultured in the bottom well of 6 (2×10$^6$ cells suspended in 3 ml) or 24 (0.5× 10$^6$ cells suspended in 0.8 ml) well Transwell™ plates. A collagen treated transwell insert (0.45 μm microporous filter) (Costar) was then placed on top of the stromal layer, and sorted DR$^-$cells plated in the upper wells (2–8 ×10$^3$ cells in 0.2 ml complete media for 24 well plates, or 4–32×10$^3$ DR$^{31}$ cells in 1 ml complete media for 6 well plates).

4. Maintenance of cultures: All cultures were maintained in a humidified atmosphere at 37° C. and 5% $CO_2$. At weekly intervals "stroma-contact" and "stroma-free" cultures were fed by removing half of the cell-free supernatant and replacing it with fresh complete media. For "stroma-non-contact" cultures, half the media from the bottom wells only was removed and replaced by fresh complete media.

5. Evaluation of long-term cultures: Non-adherent and adherent cells recovered from selected "stroma-contact" cultures after treatment with 0.15% collagenase (Boehringer Mannheim) were assayed at different time points in the short term methylcellulose assay for the presence of committed progenitors. In the short-term methylcellulose assay, the DR⁻cells were plated in clonogenic methylcellulose assay supplemented with 3 IU recombinant erythropoietin (Epoetin) (Amgen, Thousand Oaks, Calif.) and 10% conditioned media from the bladder carcinoma cell line 5637 as described by C. Verfaillie et al. Cultures were incubated in a humidified atmosphere at 37° C. and 5% $CO_2$ for 18–21 days. The cultures were assessed at day 18–21 of culture for the presence of CFU-MIX, granulocyte/-macrophage colony forming units (CFU-GM) and erythroid burst-forming units (BFU-E) as described in the C. Verfaillie et al.

Likewise, cells from selected "stroma-free" cultures or present in the upper wells of selected "stroma-non-contact" cultures were collected at different time points, enumerated under a hemocytometer, examined for their morphology and phenotype and assayed for the presence of committed or primitive progenitors. To determine phenotype, cells collected from the upper wells of transwell cultures were analyzed at week 5 of culture for the presence of $CD34^+$/HLA-DR$^+$ and $CD34^+$/HLA-DR$^-$ cells. Cells were labeled with anti-CD34-PE antibody (Becton-Dickinson) and anti-HLA-DR-FITC antibody (Becton-Dickinson). Cells were analyzed for the expression of these antigens on a FACS-Star-Plus flow cytometry system, equipped with a Consort computer. PE and FITC coupled isotype-matched mouse immunoglobulins were used as controls.

To carry out limiting dilution assays (LDA), at day zero DR⁻cells (24 replicates per concentration) (experiment 1–3: 1000, 333, 111 or 33; experiment 4: 500, 200, 100 or 20; experiment 5–6: 400, 150, 50, 15 DR⁻ cells/well) were plated onto $3 \times 10^4$ irradiated allogeneic stromal cells, subcultured in 96 well plates (Costar) (day-0 limiting-dilution assay=LDA). See H. J. Sutherland, et al., Blood, 78, 666 (1991) and PNAS USA, 87, 2584 (1990). Likewise, cells recovered after 5 weeks from collagenase treated "stroma-contact" cultures or transwell-inserts of "stroma-non-contact" cultures initiated at day 0 with 35,488 (experiments 1–3), 19,680 (experiments 4–6) or 14,760 (experiments 5–6) DR⁻cells were plated in LDA (cell number=the equivalent of 1,000, 333, 111 and 33 (experiments 1–3), 500, 200, 100, or 20 (experiment 4) or 400, 150, 50, 15 (experiments 5–6) DR⁻cells at day 0; 23±1 replicates per concentration). Stromal layers used to perform LDA at day 0 and at day 35 after initial culture in "stroma-contact" or "stroma-non-contact" cultures were derived from bone marrow samples from the same allogeneic donor. Cultures were maintained in a humidified atmosphere, at 37° C. and 5% $CO_2$ and fed weekly with 75 µl fresh media. At week 5, non-adherent and adherent cells were collected as described in C. Verfaillie, et al. and evaluated for the presence of committed progenitors. The absolute number of LTBMC-IC present in the different cell populations was calculated as the reciprocal of the concentration of test cells that gave 37% negative cultures using the Poisson statistics (E. H. Porter et al., J. Cancer, 17, 583 (1963)) and the weighted mean method (C. Taswell, J. Immunol., 126, 1614 (1981)).

Results of experimental points obtained from multiple experiments were reported as the mean ±1 standard error of the mean (SEM). Significance levels were determined by two-sided students t-test analysis.

DR⁻cells were suspended in fetal calf serum, horse serum and hydrocortisone containing media but without exogenous cytokines. Cell suspensions were plated either without stromal layer ("stroma-free"), directly onto allogeneic irradiated stromal layers ("stroma-contact") or in transwell-inserts which separated DR⁻cells from the stroma by a 0.45 µm microporous collagen-coated membrane allowing free passage of diffusible factors but preventing cell-cell contact ("stroma-non-contact") as shown in FIG. 1. These translucent transwell inserts were placed one mm above the stromal layer which was adherent to the bottom well but remained completely separated from the transwell inserts throughout the culture period. Repeated visual inspection demonstrated that no adherent stromal layer was formed in "stroma-free" cultures nor in the transwell inserts of "stroma-non-contact" cultures.

Figure 2A:
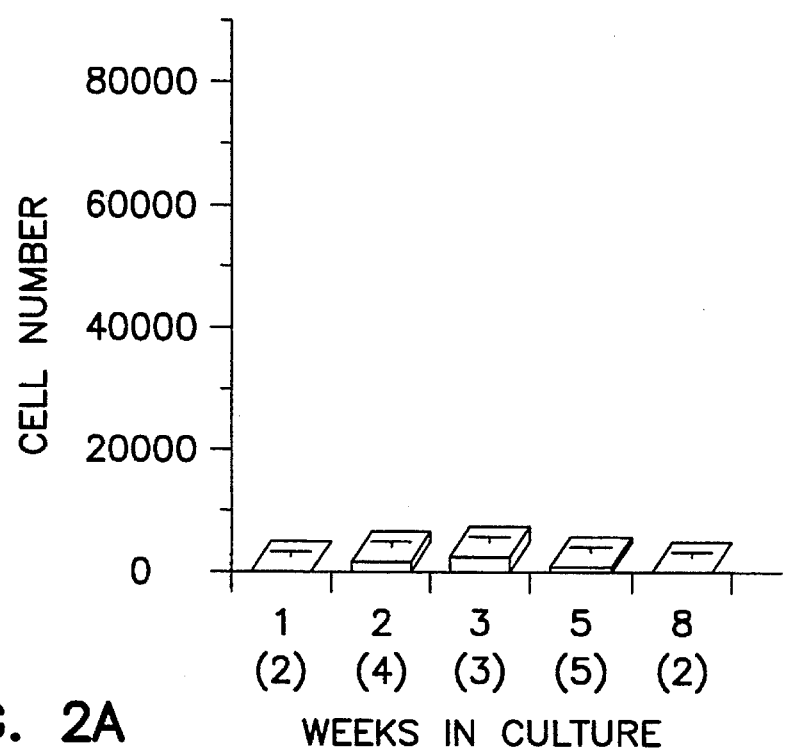
FIGS. 2A and 2B are graphic depictions of the extent of proliferation of $DR^-$ stem cells in "stroma free" and "stroma-non-contact" cultures. The data represent the mean ±SEM cell number present in cultures initiated with 5,000 $DR^-$ cells. (x)Number between brackets on the X-axis represent the number of experiments.
Figure 2B:
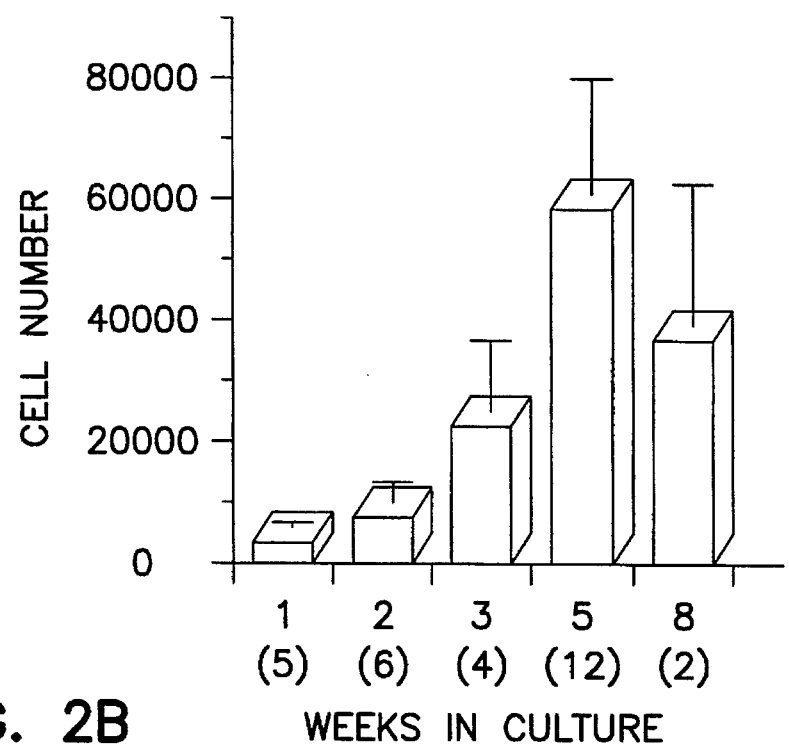

When DR⁻cells were plated in the absence of a stromal layer ("stroma-free"), a progressive decline in cell number is observed (FIG. 2). Virtually all cells were monocytes at week 2. In contrast, serial evaluation of "stroma-non-contact" cultures revealed that, after an initial decline in cell number at week 1, the cell number in the transwell-inserts increased steadily (FIG. 2). At week 1, more than 55% of cells were blasts admixed with promyelocytes. Over the next 4 weeks, the percentage of blasts declined; the percentage of promyelocytes remained constant and a gradual increase in mature myeloid elements was seen. At week 8, blasts and myeloid precursors decreased further with a reciprocal increase in monocytes. FACS analysis of cells present in "stroma-non-contact" cultures at week 5 demonstrated that 4.1±1.2% of cells were $CD34^+$/HLA-DR$^+$(n=6) associated with more differentiated hematopoietic progenitors, and 1.1±0.16% of cells remained $CD34^+$/HLA-DR$^-$(n=6). Taking into account that the total cell number was 8±3.8 fold higher at week 5 compared with day 0, these studies demonstrate that for each DR⁻cell used to initiate the cultures 19±5 $CD34^+$/HLA-DR$^+$cells were generated and approximately 6% of DR⁻cells could be conserved for a minimum of 5 weeks.

These experiments demonstrate that, although stroma is important for in vitro hematopoiesis, direct contact between stem cells and the stromal layer is necessary neither for the differentiation of such progenitors into more differentiated 34$^+$/DR$^+$cells and mature myeloid cells, nor for the conservation of a fraction of primitive 34$^+$/DR$^-$progenitors.

To test this hypothesis further, cells recovered from "stroma-free," "stroma-contact" and "stroma-non-contact" were plated in cultures in the methylcellulose progenitor assay to evaluate the production of clonogenic cells. As demonstrated by the data summarized in Table 1, very few clonogenic cells were present in "stroma-free" cultures during the first 3 weeks, while none were present in such cultures at weeks 5 and 8.

TABLE 1

Recovery of committed progenitors from primitive DR⁻ cells culture in "stroma-free," "stroma-contact" and "stroma-non-contact" cultures.

| CULTURE | WEEK (n=) | CFC | CFU-GM | BFU-E |
|---|---|---|---|---|
| Sorted DR⁻ cells | 0 (5) | 66.4 ± 13.9 | 25.5 ± 1.65 | 40.9 ± 12.6 |
| "Stroma-free" | 1 (3) | 12.2 ± 5.1 | 8.8 ± 1.8 | 3.3 ± 3.3 |
| | 2 (4) | 4.2 ± 3.2 | 1.8 ± 1.2 | 2.5 ± 2.5 |
| | 3 (2) | 13.3 ± 0 | 13.3 ± 0 | 0 ± 0 |
| | 5 (4) | 0 ± 0 | 0 ± 0 | 0 ± 0 |
| | 8 (2) | 0 ± 0 | 0 ± 0 | 0 ± 0 |
| "Stroma-contact" | 1 (4) | 81.7 ± 10 | 39.3 ± 8.1 | 45.3 ± 9.9 |
| | 2 (5) | 85.8 ± 17.7 | 53.7 ± 12.1 | 35.7 ± 7.7 |
| | 3 (2) | 96.3 ± 23.3 | 58.3 ± 15 | 38.3 ± 8.3 |
| | 5 (12) | 150 ± 16.7 | 108 ± 23 | 44.1 ± 9.8 |
| | 8 (2) | 47.8 ± 1.8 | 34.95 ± 1.65 | 13.3 ± 3.3 |
| "Stroma-non-contact" | 1 (4) | 107.5 ± 15* | 88.8 ± 8.8* | 25.4 ± 4.2 |
| | 2 (5) | 126.8 ± 30* | 86.4 ± 28.8* | 31.8 ± 9.7 |
| | 3 (2) | 165.7 ± 79 | 154 ± 74 | 9.5 ± 2.5 |
| | 5 (12) | 333 ± 41†* | 273 ± 37†* | 28.3 ± 9.8* |
| | 8 (2) | 99.6 ± 19.6* | 98 ± 18†* | 1.6 ± 1.6 |

NO. OF COLONIES PER 5,000 DR⁻ CELLS[a]

[a]Colonies were enumberated at day 14–19 (CFC = colony forming cells; CFU-GM = granulocyte-macrophage colony-forming-unit; BFU-E = erythroid burst-forming-unit). Results are the mean number ± SEM of colonies obtained from 5,000 DR⁻ cells.
(x): Values between brackets represent the number of experiments. Students t-test:
*: $p \leq 0.01$: Comparison between "stroma-free" and "stroma-non-contact" cultures.
†: $p \leq 0.01$: Comparison between "stroma-contact" and "stroma-non-contact" cultures.

"Stroma-contact" cultures yielded an increasing number of clonogenic cells over the first 5 weeks with a decrease in committed progenitor recovery by week 8. When DR⁻cells were plated in "stroma-non-contact" culture, a similar increase was observed in the generation of committed progenitors during the first 5 weeks, which declined by week 8. These studies demonstrated that bone marrow derived stromal cells are required for the proliferation and differentiation of primitive hematopoietic progenitors when no exogenous cytokines are provided. However, induction of differentiation does not require direct contact between the hematopoietic progenitors and the stromal layer, suggesting that diffusible factors are released from the stromal environment that induce differentiation of primitive progenitors placed in a transwell-insert 1 mm above the stromal layer.

"Stroma-non-contact" cultures also differed from "stroma-contact" cultures in that a significantly greater number of CFU-GM were recovered from "stroma-non-contact" cultures at weeks 5 and 8 compared with "stroma-contact" cultures (Table 1). This indicates that in contrast to differentiation-inducing factors, negative regulators of stem cells are either not released or reach the cultured stem cells in lower concentrations in "stroma-non-contact" cultures. Alternatively, direct hematopoietic cell-stroma interaction may actually be required to convey differentiation-inhibiting signals.

Example 2. Self-Renewal of Stem Cell Populations

D. Zipori et al., *Exp. Hematol.*, 6, 816 (1980) have postulated that one of the major roles of stromal tissue may be to maintain the most primitive progenitor ("stem cell") compartment. Removal of the close cell-cell interactions between hematopoietic and stromal cells could, therefore, induce differentiation only and result in an accelerated exhaustion of the stem cell pool (L. Siminovich et al., *J. Cell. Comp,. Physiol.*, 64, 23 (1964)). In order to test this possibility, 6 separate experiments were conducted to compare the absolute number of stem cells capable of initiating long-term bone marrow cultures (LTBMC-IC) still present after culture of DR⁻cells for 5 weeks in "stroma-contact" or "stroma-non-contact" cultures with the absolute number of LTBMC-IC present in the FACS sorted DR⁻population. The results of these experiments are summarized in Table 2, below.

TABLE 2

Stem cells are conserved equally well when primitive DR⁻ cells are cultured in "stroma-contact" and "stroma-non-contact" cultures.

ABSOLUTE NUMBER OF LTBMC-IC SORTED DR⁻ CELLS[a]

| Experiment | Sorted DR⁻ cells | "Stroma-contact" | "Stroma-non-contact" |
|---|---|---|---|
| 1 | 1/73 | 1/415 | 1/180 |
| 2 | 1/204 | 1/825 | 1/251 |
| 3 | 1/132 | 1/480 | 1/283 |
| 4 | 1/102 | 1/303 | 1/168 |
| 5 | 1/68 | 1/600 | 1/208 |
| 6 | 1/168 | — | 1/349 |
| Mean ± SEM | 1/123 ± 22* | 1/524 ± 89† | 1/239 ± 28 |

[a]The absolute number of LTBMC-IC present in the different cell populations was calculated as the reciprocal of the concentration of test cells that gave 37% negative cultures using the Poisson statistics and the weighted mean method.
*: $p = 0.001$ and $p = 0.009$: Comparison between day 0 LDA and "stroma-contact" and "stroma-non-contact" cultures respectively.
†: $p = 0.009$: Comparison between "stroma-contact" and "stroma-non-contact" cultures.

As shown by the data summarized on Table 2, one LTBMC-IC per 123±22 sorted DR⁻cells was present at day 0. When DR⁻cells were cultured for 5 weeks in either "stromacontact" culture (1LTBMC-IC per 524±89 initially sorted DR⁻cells; p=0.001) or "stroma-non-contact" culture (1 LTBMC-IC per 239±28 initially sorted DR⁻cells; p=0.009) and then assessed for their stem cell content, a decrease in absolute number of LTBMC-IC was observed. (Table 2.) However, the decrease in stem cells capable of initiating long-term in vitro hematopoiesis was significantly greater in "stroma-contact" than in "stroma-non-contact" cultures (p=0.009). Thus, the present method eliminates the need to provide direct hematopoietic cell-stroma contact to maintain a fraction of pluripotent stem cells which are capable of initiating in vitro hematopoiesis. Surprisingly, culture of normal stem cells separated from the adherent stromal layer results in an increased generation of committed granulocyte-macrophage progenitors and conserves stem cells with long-term in vitro repopulating capacity better than culture of stem cells in direct contact with the stromal layer.

Example 3. Stromal-Non-Contact Cultures Plus Added Cytokines

Sorted Lin⁻34⁺DR⁻stem cells were cultured in transwell inserts above irradiated human stromal cells as described in Example 1 (1–5 ml wells). Recombinant human interleukin-3 (5 ng/ml) (IL-3) alone or in combination with 100 ng/ml macrophage inflammatory protein-1α (MIP-1α, R. D. Systems, Minneapolis, Minn.) was added three times per week to the cultures. Additional cultures received 5 ng/ml IL-3 on day 0 and 2 after feeding, and TGF-β (10 ng/ml) on day 4 after feeding. After five weeks, cells recovered from the transwells were enumerated and replated in methylcellulose assay to determine the CFC, or on secondary stromal layers in limiting dilution assay (LDA) to determine the absolute number of LTBMC-IC. On day 0, freshly sorted DR⁻cells were also plated in LDA onto stromal layers to provide a measure of the initial LTBMC-IC. The results of these assays are summarized on Table 3, below.

TABLE 3

| Cytokine | Cell Expansion (1) | CFC(L) | LTBMC-IC(2) |
| --- | --- | --- | --- |
| None | 100 ± 0% | 100 ± 0% | 44 ± 5%¥ |
| IL-3 | 1400 ± 480%* | 220 ± 45%* | 52 ± 8%¥ |
| IL-3 + TGF-β | 320 ± 49%¶ | 72 ± 15% | 12 ± 2.4%¥¶ |
| IL-3 + MIP-1α | 1780 ± 480%* | 248 ± 25%¶ | 122 ± 14%¶ |

(1): compared with cytokine-free cultures. $p < 0.05(*)$; $p < 0.01(\P)$
(2): compared with day 0 LDA (= 100 ± 0%); $p < 0.001$ ¥

As shown by the data in Table 3, IL-3 alone and in combination with MIP-1α, but not with TGF-β, resulted in a significantly greater cell expansion and generation of CFC than did cytokine-free cultures. Culture of DR⁻cells for five weeks in cytokine-free transwell cultures resulted in a 56% loss of LTBMC-IC compared with FACS sorted DR⁻cells (day 0). Addition of IL-3 to transwell cultures also resulted in a small but consistent increase in LTBMC-IC recovery after five weeks of culture compared with cyto-kine-free cultures whereas addition of IL-3+TGF-β resulted in a significantly greater loss of LTBMC-IC. Surprisingly, combined addition of IL-3+MIP-1α resulted in a significantly greater recovery of LTBMC-IC compared with non-supplemented cultures. Moreover, the absolute number of LTBMC-IC present in cells recovered from IL-3+ MIP-1α supplemented cultures was either equivalent or greater than that present in the freshly sorted DR⁻population used to initiate the transwell cultures on day 0 (93%, 135% and 136% of day 0 LDA). In conclusion, this example demonstrates for the first time that stem cells (LTBMC-IC) can be conserved/expanded in vitro. This requires soluble factors produced by cultured human irradiated stromal cells in combination with IL-3 and MIP-1α.

Example 4. Use of Stromal Cell Lines

Sorted DR⁻cells were cultured in transwell inserts positioned above irradiated allogeneic bone marrow-derived stromal cell layers as described in Example 1 (1 or 5 ml wells). However, DR⁻cells were also plated in transwell inserts positioned above irradiated (6,000 rad) stromal feeder cells consisting of the murine stromal cell line M210B4 (C. Eaves et al., *Blood,* 78, 666 (1991)) ("M210B4 feeder cultures") or the murine stromal cell line NIH-3T3 (ATCC Accession No. 1658, Rockville, Md.).

Cell expansion, generation of CFC and conservation of LTBMC-IC were evaluated at week 5 and compared with that seen in "stroma-non-contact" cultures which had not been supplemented with cytokines. As shown by the data in Table 4, these experiments demonstrate that: (1) cell expansion is similar in "murine feeder" cultures as in "stroma-non-contact" cultures; (2) generation of CFC is similar in "murine feeder" cultures as in "stroma-non-contact" cultures; and (3) conservation of LTBMC-IC is similar in "murine feeder" cultures as in "stroma-non-contact" cultures.

TABLE 4

Comparison of M210B4 or NIH-3T3 Cell Line With Normal Allogeneic Stromal Feeders

| | Murine M210B4 | Murine NIH-3T3 |
| --- | --- | --- |
| Cell Expansion (Fold) | 95 ± 11% (n = 8) | 67 ± 4% (n = 8); $p \leq 0.001$ |
| CFC/5,000 DR⁻ cells | 91 ± 13% (n = 8) | 80 ± 8% (n = 8) |
| LTBMC-IC | 119 ± 26% (n = 4) | 64 ± 15% (n = 5); $p = 0.05$ |

Example 5

Figure 3:
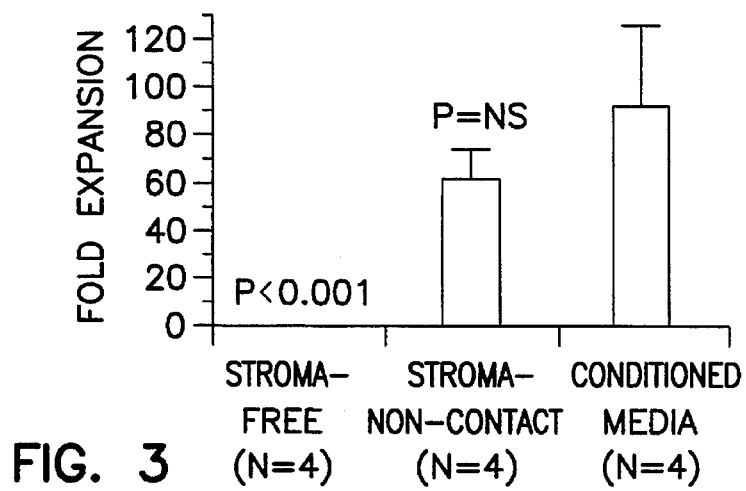
FIG. 3 is a graphical depiction of the expansion of $DR^-$ cells in "stroma-free,", "stroma-non-contact" and "conditioned media" cultures.
Figure 4:
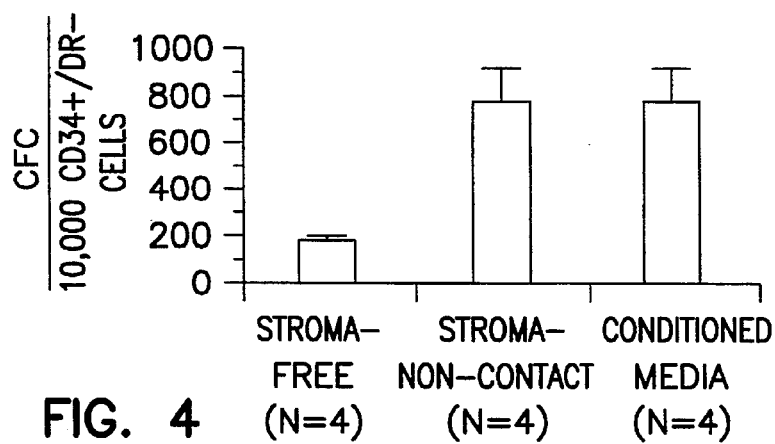
FIG. 4 is a graphical depiction of the generation of colony-forming cells (CFC) in "stroma-contact," "stromal-non-contact" and "conditioned medium" cultures.
Figure 5:
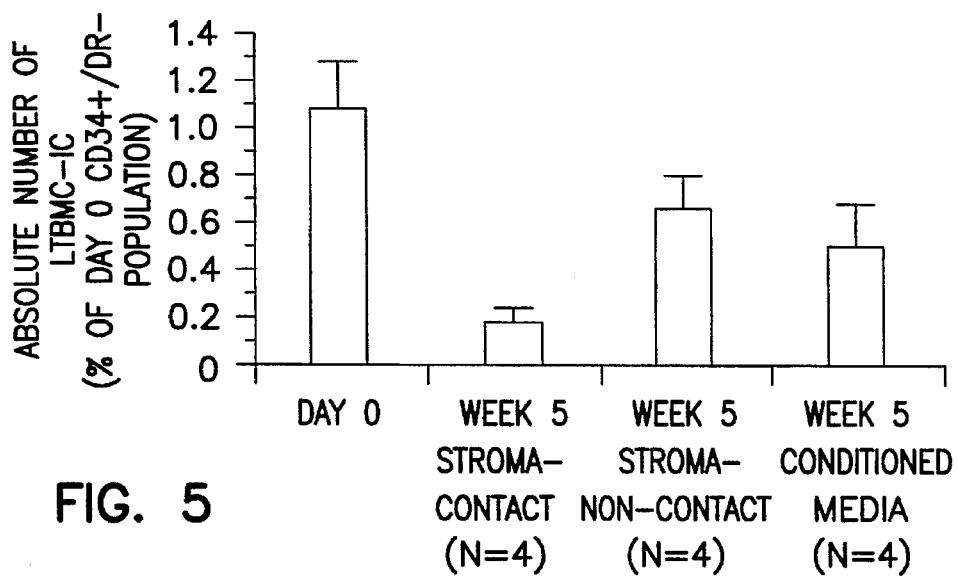
FIG. 5 is a graphical depiction of the 5-week maintenance of LTBMC-IC by "stroma-contact," "stroma-non-contact" and "conditioned media" cultures.

Sorted DR⁻cells obtained as described hereinabove were plated in collagen-treated transwell inserts (Costar). (2–5× $10^3$ cells in 1 ml complete media using 24 well plates). Irradiated allogeneic stromal cells were cultured in the bottom of separate 6 well plates or T75 flasks (0.35 ×$10^6$ cells) in five ml complete medium. All cultures were maintained in a humidified atmosphere at 37° C. and 5% $CO_2$. Once a day for 35 days one ml of media was removed from the stromal cell culture vessel and used to replace an equivalent volume of culture media taken from the well containing the cultured DR⁻cells in the transwell inserts. The volume removed initially was replaced with fresh medium. The stromal cell medium was also 50% replaced every seven days. After five weeks, the cultured cells were replated in short-term methylcellulose culture to enumerate colony-forming cells (CFC); or replated onto cultured stromal cell layers in a limiting dilution assay (LDA) to determine the absolute number of LTBMC-IC. As shown in FIGS. 3–5, it was found that: (1) cell expansion is similar in "conditioned media" cultures as in "stroma-non-contact" cultures of Example 1(3) (FIG. 3); (2) generation of CFC is similar in "conditioned media" cultures as in "stroma-non-contact" cultures (FIG. 4); and (3) conservation of LTBMC-IC is similar in "conditioned media" cultures as in "stroma-non-contact" cultures (FIG. 5).

Example 6. Hollow Fiber Culture of Lin⁻/CD34⁺ Bone Marrow Cells

Lineage⁻/CD34⁺bone marrow progenitor cells were obtained as described in the materials and methods section, above, but were not sorted to yield DR⁻cells. A hollow fiber culture system, commercially available from Cell Co. Inc., Germantown, Md., was employed, which comprises a reservoir containing 70 ml of complete media, and two hollow fiber bundles, 0.5 μm pore size, contained in separate reservoirs. About 4×$10^6$ Lin⁻/CD34⁺cells were loaded on the outside of one of the fiber bundles and about 5×$10^6$ of irradiated M210B4 murine stromal feeder cells were loaded on the outside of the other fiber bundle. The reservoirs were then filled with culture media and media was circulated from the reservoir and through the hollow fiber bundles at one ml/minute under ambient conditions.

Cell expansion, generation of colony-forming cells (CFC) and conservation of LTBMC-IC were evaluated after five weeks of culturing and the results compared with those from stromal non-contact cultures which had not been supplemented with cytokines (Table 5).

TABLE 5

| | Cell Expansion | CFC (fold increase) | LTBMC-IC (fold increase) |
|---|---|---|---|
| Day 0 | — | 214/10,000 CD34+ cells | 16.6/10,000 CD34+ cells |
| M210B4 Feeder (Transwell) | 15 fold | 243/10,000 CD34+ cells (1.14 fold) | 8.325/10,000 CD34+ cells (.5 fold) |
| Hollow Fiber System (M210B4) | 10 fold | 298/10,000 CD34+ cells (1.39 fold) | 10.6/10,000 CD34+ cells (.63 fold) |

As demonstrated by the data in Table 5, there is (1) a 10–15 fold expansion of cells in either culture system; (2) significant numbers of CFC can be recovered from either culture at five weeks; and (3) 50% of LTBMC-IC present in the original inoculum can be maintained using either culture system for five weeks.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A cell culture method comprising culturing in vitro a population of human hematopoietic cells comprising stem cells or committed progenitor cells supported in a non-contacting relationship to a supported population of cultured stromal cells, which said populations are in a body of liquid stromal cell culture medium comprising an effective stimulatory amount of IL-3 and macrophage inflammatory protein-1α (MIP-1α) added thereto, so that the ability of the stem cells to self-replicate and differentiate is maintained or the ability of the committed progenitors to expand and differentiate is maintained.

2. The method of claim 1 wherein the hematopoietic cells consist essentially of committed progenitor cells.

3. The method of claim 1 wherein the hematopoietic cells comprise stem cells.

4. The method of claim 1 wherein the hematopoietic cells are derived from bone marrow cells.

5. The method of claim 1 wherein the hematopoietic cells are derived from peripheral blood or from newborn cord blood.

6. The method of claim 1 wherein the stem cells are $CD34^+$.

7. The method of claim 6 wherein the stem cells are $Lin^- CD34^+ DR^-$.

8. The method of claim 1 wherein the stromal cells are human stromal cells or murine stromal cells.

9. The method of claim 1 wherein the hematopoietic cell population and the stromal cell population are cultured on discrete and separable cell culture substrata.

10. The method of claim 1 wherein the hematopoietic cell population is supported on a microporous membrane.

11. The method of claim 10 wherein the hematopoietic cell population is supported on a microporous membrane, which said membrane separates the stromal cell population from the hematopoietic cell population.

12. The method of claim 11 wherein the stromal cell population is adhered to the bottom of a plastic cell culture well.

13. The method of claim 1 wherein the hematopoietic cell population and the stromal cell population are separated by about 0.25–2 mm.

14. The method of claims 1 or 9 wherein the liquid stromal cell growth medium is 25–100% exchanged at intervals of about 8 hrs–14 days.

15. The method of claim 9 wherein the liquid stromal cell growth medium is continuously circulated through a first chamber comprising said stromal cells and a second chamber comprising said hematopoietic cells.

16. The method of claim 15 wherein the hematopoietic cell population and the stromal cell population are adhered to the outside of discrete hollow fibers.

17. The method of claim 1 wherein the populations are allogeneic.

18. The method of claim 1 wherein the populations are autologous.

* * * * *

UNITED STATES PATENT AND TRADEMARK OFFICE
CERTIFICATE OF CORRECTION

PATENT NO. : 5,460,964

DATED : October 24, 1995

INVENTOR(S) : McGlave et al.

It is certified that error appears in the above-indentified patent and that said Letters Patent is hereby corrected as shown below:

Column 12 Line 54-55 Please delete "as described C. Veraillie et. al. (FIG. 1B)" therefor.

Signed and Sealed this

Twenty-sixth Day of November 1996

Attest:

BRUCE LEHMAN

*Attesting Officer*     *Commissioner of Patents and Trademarks*